(12) United States Patent
McTavish

(10) Patent No.: US 6,410,258 B1
(45) Date of Patent: *Jun. 25, 2002

(54) MOLECULAR HYDROGEN PRODUCTION BY DIRECT ELECTRON TRANSFER

(76) Inventor: Hugh McTavish, 1215 Englewood Ave., St. Paul, MN (US) 55104

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/879,920

(22) Filed: Jun. 20, 1997

(51) Int. Cl.[7] .................................................. C12P 3/00
(52) U.S. Cl. ..................... 435/41; 530/350; 435/170; 435/173; 435/262; 423/648.1; 423/657; 204/157.15
(58) Field of Search ................................ 530/300, 350; 423/644, 648.1, 652, 657; 435/41, 262, 170, 173; 204/157.15

(56) References Cited

PUBLICATIONS

McTavish, J. Biochem (Tokyo) vol. 123, 644–649, 1998.*
Krasnovsky Et Al., "Efficiency of Hydrogen Production by Chloroplast–Bacterial Hydrogenase Systems" Plant Physiol, (1980), v66(5), pp. 925–930.*
Adams, "The structure and mechanism of iron–hydrogenases", Biochim, Biophys. Acta, 1020, 115–145 (1990).
Arnon, "Copper Enzymes in Isolated Chloroplastes. Polyphenoloxidase in Beta Vulgaris", Plant Physiol., 24, 1–15 (1949).
Benemann et al., "Hydrogen Evolution by a Chloroplast–Ferredoxin–Hydrogenase System", Proc. Nat. Acad. Sci., USA, 70, 2317–2320 (1973).
Bradford, "A Rapid and Sensitive Method for the Quantitation of Microgram Quantities of Protein Utilizing the Principle of Protein–Dye Binding", Anal. Biochem., 72, 248–254 (1976).
Evans et al., "The Oxidation–Reduction Potential of the Reaction–Centre Chlorophyll (P700) in Photosystem I", Biochem. J., 162, 75–85 (1977).
Friedrich et al., "Molecular Biology of Hydrogen Utilization in Aerobic Chemolithotrophs", Annu. Rev. Microbiol., 47, 351–383 (1993).
Golbeck et al., "Photosystem I", Curr. Topics Bioenergetics, 16, 83–177 (1991).
Greenbaum et al., "$CO_2$ fixation and photoevolution of $H_2$ and $O_2$ in a mutant of Chlamydomonas lacking photosystem I", Nature, 376, 438–441 (1995).
Heathcote et al. "The Role of the Membrane–Bound Iron–Sulphur Centres A and B in the Photosystem I Reaction Centre of Spinach Chloroplasts", Biochim. Biophys. Acta, 503, 333–342 (1978).
Hoffman et al., "Photosynthetic Hydrogen Evolution by Spinach Chloroplasts Coupled to a Clostridium Hydrogenase", Z. Naturforsch, 32c, 257–262 (1977).
Klein et al., "Fermentative Metabolism of Hydrogen–evolving Chlamydomonas moewusii[1]", Plant Physiol., 61, 953–956 (1978).
Krishna et al., "Hydrogen evolution by chloroplast–hydrogenase systems: improvements and additional observations", Biochimie, 60, 291–296 (1978).
Kuwabara et al., "Inactivation of Photosynthetic Oxygen Evolution and Concomitant Release of Three Polypeptides in the Photosystem II Particles of Spinach Chloroplasts", Plant & Cell Physiol., 23, 533–539 (1982).
Li et al., "PsaD Is Required for the Stable Binding of PsaC to the Photosystem I Core Protein of Synechococcus sp. PCC 6301[+]", Biochem., 30, 7863–7872 (1991).
Markov et al., "The Potential of Using Cyanobacteria in Photobioreactors for Hydrogen Production", Adv. Biochem. Engineer. Biotech., 52, 60–86 (1995).
Marsho et al., "P700 Detection", Meth. Enzymol., 69, 280–289 (1980).
Przybyla et al., "Structure–function relationships among the nickel–containing hydrogenases", FEMS Microbiol. Rev., 88, 109–135 (1992).
Rosen et al., "Limiting Reactions in Hydrogen Photoproduction by Chloroplasts and Hydrogenase", Photochem. Photobiol., 31 259–265 (1980).
Schneider et al. "Content and localization of FMN, Fe–S clusters and nickel in the NAD–linked hydrogenase of Nocardia opaca 1b", Eur. J. Biochem., 142, 75–84 (1984).
Sweet et al., "Polarographic Measurement of $H_2$ in Aqueous Solutions", Anal. Biochem., 107, 337–340 (1980).
Vatsala et al., "Microbial Production of Hydrogen—A Review", Proc. Indian Nat'l Sci. Aca., B51, 282–295 (1985).
Wu et al., "Microbial hydrogenases: Primary structure, classification, signatures and phylogeny", FEMS Microbiol. Rev., 104, 243–269 (1993).
Wynn et al., "Characterization of an isolated chloroplast membrane Fe–S protein and its identification as the photosystem I $Fe-S_A/Fe-S_B$ binding protein", FEBS Lett., 229, 293–297 (1988).
L.E. Mortenson, "Purification and Analysis of Ferredoxin From Clostridium Pasteurianum", Biochim. Biophys. Acta, 81, 71–77 (1964).
D.A. Walker, "Chloroplasts (and Grana): Aqueous (Including High Carbon Fixation Ability)", Meth. Enzym., 23, 211–220 (1971).
Rabinowitz, "Preparation and Properties of Clostridial Ferredoxins", Methods in Enzymology, 24, 431 (1972).
Buchanan and Arnon, "Ferredoxins for Photosynthetic Bacteria, Algae, and Higher Plants", Methods in Enzymology, 23, 413 (1971).

* cited by examiner

Primary Examiner—Christopher S. F. Low
Assistant Examiner—David Lukton

(57) ABSTRACT

The present invention discloses a method for making hydrogen with biological components including photosystem I complex from a photosynthetic organism and a hydrogenase enzyme in the absence of an intervening exogenous electron carrier.

18 Claims, 2 Drawing Sheets

MOLECULAR HYDROGEN PRODUCTION BY DIRECT ELECTRON TRANSFER

STATEMENT OF GOVERNMENT SUPPORT

This invention was made with government support under U.S.D.A. grant No. 94-37500-1073 awarded by the U.S. Department of Agriculture. The government may have certain rights in the invention.

FIELD OF THE INVENTION

The present invention relates to biological hydrogen production. More specifically, the present invention relates to a process for employing the components of photosynthetic organisms, to use light energy to make molecular hydrogen.

BACKGROUND OF THE INVENTION

Aerobic oxygen-producing photosynthetic organisms, or subcellular components from such organisms, have been used previously to make hydrogen gas (Benemann et al., *Proc. Nat. Acad. Sci. USA* 70:2317, 1973, Rosen and Krasna, *Photochem. Photobiol.* 31:259, 1980, Rao et al, *Biochimie* 60:291, 1978).

The components of cell-free (i.e., in vitro) systems reported in these references require isolated thylakoids or solubilized photosystem I (PSI) from thylakoids; an electron donor, such as water or an artificial electron donor such as dithiothreitol or ascorbic acid; a hydrogenase capable of accepting electrons from photosystem I that can catalyze the combination of 2 electrons and 2 protons to form molecular hydrogen when electrons are received from an electron donor that can be oxidized by the hydrogenase; and an exogenous electron carrier that is capable of accepting electrons from photosystem I and can donate electrons to the hydrogenase. Examples of exogenous electron carriers that have been used as electron donors to the hydrogenase include ferredoxin and cytochrome $c_3$ and the dye methyl viologen.

The biochemical pathway for molecular hydrogen production from elemental hydrogen is known. An electron on photosystem I (either isolated photosystem I or photosystem I in thylakoids) is excited, typically by light, to a higher energy (lower redox potential) resulting in the donation of an electron to an exogenous electron carrier that in turn can transfer electrons to the enzyme hydrogenase. In this process, oxidized photosystem I can then extract an electron from an electron donor, either directly or through an electron transfer chain, such as that found in the thylakoid membrane. Where water acts as the electron donor, the electron transfer chain includes photosystem II. Meanwhile, two reduced electron carrier molecules (having been reduced by illuminated photosystem I) are able to donate electrons to the enzyme hydrogenase. Hydrogenase combines two electrons with two protons to form a hydrogen molecule.

The yield of molecular hydrogen from this process is limited because the exogenous electron carriers donate their electrons to destinations other than hydrogenase. For example, reduced electron carriers, such as ferredoxin and methyl viologen, will react with oxygen to form superoxide and hydrogen peroxide. This results in lost reducing power and decreased molecular hydrogen yield. Even in the absence of oxygen, this system is still inefficient because exogenous electron carriers in this system oxidize to a large extent without reacting with hydrogenase (Rosen and Krasna, *Photochem. Photobiol.* 31:259, 1980). Exogenous electron carriers can be oxidized by oxidized photosystem I itself to produce what is known as cyclic electron transfer. This results in the oxidation of the exogenous electron carriers. Any other enzymes or chemicals present that are capable of oxidizing the exogenous electron carriers could also compete with hydrogenase for those electrons, decreasing the yield of molecular hydrogen.

It is believed that exogenous electron carrier molecules are necessary to catalyze the electron transfer from photosystem I to hydrogenase. Perhaps because of that belief, low concentrations of thylakoids (or photosystem I) and hydrogenase have been used for in vitro hydrogen gas production. For example, thylakoids containing fifty micrograms ($\mu$g) of chlorophyll per ml or approximately 0.05 micromolar ($\mu$M) photosystem I was used for light-dependent molecular hydrogen production in Rao et al. (supra), and 0.7 units of hydrogenase per ml were used by Benemann et al. (supra).

A small amount of molecular hydrogen production has been observed in vitro in the absence of an exogenous electron carrier (Rosen and Krasna, *Photochem. Photobiol.* 31:259, 1980). This work did not include the use of a purified hydrogenase; rather, crude extracts of *Clostridium pasteurianum* were used in place of a purified enzyme. These systems contain a large amount of ferredoxin, a known exogenous electron carrier and, indeed, the authors attributed hydrogen production to ferredoxin contamination. This explanation is further supported by the fact that the system of Rosen and Krasna (supra) would have contained much more ferredoxin than hydrogenase in the *C. pasteurianum* extracts.

Hoffman et al. (*Z. Naturforsch* 32c:257, 1977) have also reported a small amount of light-driven molecular hydrogen production from an in vitro system using thylakoids and hydrogenase from *C. pasteurianum*. Here, the rate of light-driven hydrogen production increased linearly with rising exogenous electron carrier concentration and could be extrapolated approximately to zero at zero added exogenous electron carrier (see FIG. 2, of that reference). Again, the small amount of hydrogen production observed in this system without an exogenous electron carrier could be explained, as above, by ferredoxin contamination of either thylakoids or hydrogenase.

At least two groups of oxygen-producing photosynthetic organisms are capable of producing hydrogen in vivo. These include cyanobacteria and green algae. Cyanobacteria generally use the enzyme nitrogenase to produce molecular hydrogen. Electrons used in this molecular hydrogen-producing process are derived from stored carbohydrate and are used to reduce ferredoxin, which is the immediate electron donor for nitrogenase (reviewed by Markov et al. *Advances in Biochemical Engineering and Biotechnology* 52:60, 1995). Hydrogenase can also catalyze molecular hydrogen production in cyanobacteria (supra). In most cases the electrons for molecular hydrogen production are obtained from stored carbohydrate. In cyanobacteria, molecular hydrogen production is inhibited by oxygen and/or light. Light-dependent hydrogenase-mediated molecular hydrogen production occurs in *Oscillatoria limnetica* in photosystem I-dependent reactions when the cells are in the presence of sulfide, which inactivates photosystem II and prevents oxygen production. The pathway of electron transfer from photosystem I to hydrogenase is unknown.

Green algae can also photoevolve (i.e., produce) molecular hydrogen via hydrogenase. The pathway of electron transfer is again unknown and in one case does not depend on photosystem I (Greenbaum et al. *Nature* 376:438, 1995). The source of electrons for the process has been shown to be endogenously fermented carbohydrate (Klein and Betz, *Plant Physiol.* 61:953, 1978). Hydrogen production stops in the presence of carbon dioxide (Vatsala and Seshadri, *Proc. Indian Nat'l Sci. Acad.* B51:282, 1985), indicating that the electron sink of carbon dioxide reduction is a better competitor for photosynthetic electron flow than hydrogenase.

Molecular hydrogen has a number of commercial uses. Molecular hydrogen is used for the production of ammonia, in petroleum refining, in the food industry for hydrogenation of vegetable oils, in electronic circuitry manufacture and as a fuel, for example, for space travel. Hydrogen is an almost pollution-free fuel and when burned, hydrogen produces only water vapor. Molecular hydrogen is currently made primarily by steam reforming of natural gas but this process produces carbon dioxide.

There is a need for new methods for producing molecular hydrogen since steam reforming of natural gas results in the production of carbon dioxide, natural gas is not a renewable resource, and carbon dioxide has been associated with global warming.

SUMMARY OF THE INVENTION

This invention relates to methods for producing molecular hydrogen and for obtaining hydrogen gas. The process uses a hydrogenase enzyme and components of the photosynthetic apparatus from oxygen-producing photosynthetic organisms. The methods and compositions of this invention do not require an exogenous electron carrier.

In one aspect of this invention a method for producing molecular hydrogen is disclosed. The method comprises the steps of combining (a) photosystem I from a photosynthetic organism, (b) at least one hydrogenase enzyme wherein the enzyme is capable of catalyzing the production of hydrogen gas, and (c) an electron donor capable of donating electrons to photosystem I; and producing molecular hydrogen wherein molecular hydrogen production does not depend on the presence of an exogenous electron carrier. In a preferred embodiment of this aspect of the invention the photosystem I of the combining step is present in thylakoids and the electron donor includes the natural photosynthetic electron transfer process present on the thylakoid membranes. In this embodiment, the electron donor is preferably water. In one embodiment the electron donor of the combining step is capable of donating electrons indirectly to photosystem I. In a preferred embodiment, the indirect electron donor is water. In another embodiment the electron donor of the combining step is capable of donating electrons directly to photosystem I. The direct electron donors include a variety of donors including dithiothreitol, ascorbic acid, and the like.

In one embodiment, molecular hydrogen production occurs in a cell-free composition. In another embodiment, the photosystem I of the combining step is an isolated photosystem I complex. The hydrogenase of the combining step can be purified from a cell or is an isolated recombinant protein.

In one embodiment, the electron donor of the combining step is dithiothreitol, in another the electron donor of the combining step is dithionite. The electron donor can be a combination of electron donors, including, but not limited to dithiothreitol and ascorbic acid.

In one embodiment of the method of this invention, the method includes, after the combining step, the step of exposing the composition to light. The producing step can additionally comprise the step of isolating molecular hydrogen as a gas.

This invention also relates to a cell free composition capable of producing molecular hydrogen comprising: photosystem I from a photosynthetic organism; at least one hydrogenase enzyme, wherein the enzyme is capable of catalyzing the production of hydrogen gas; and at least one electron donor capable of donating electrons to photosystem I wherein molecular hydrogen production is independent of an exogenous electron carrier. In one embodiment the photosystem I is present in isolated thylakoids in the composition and in another embodiment, the photosystem I is present in the composition as an isolated complex, preferably substantially thylakoid membrane free.

In one embodiment, the hydrogenase is purified from a cell and in another embodiment, the hydrogenase is a recombinant protein. In one embodiment the electron donor is water and the photosystem I complex is present in isolated thylakoids in the composition. In another embodiment the electron donor is dithiothreitol or dithionite. In yet another embodiment, the electron donor is a combination of dithiothreitol and ascorbic acid.

In one embodiment of this composition capable of producing molecular hydrogen, the combination is exposed to light and in another embodiment, for example, where the electron donor is dithionite, the composition capable of producing molecular hydrogen is maintained in the dark.

DETAILED DESCRIPTION OF THE PREFERRED EMBODIMENTS

Figure 1:
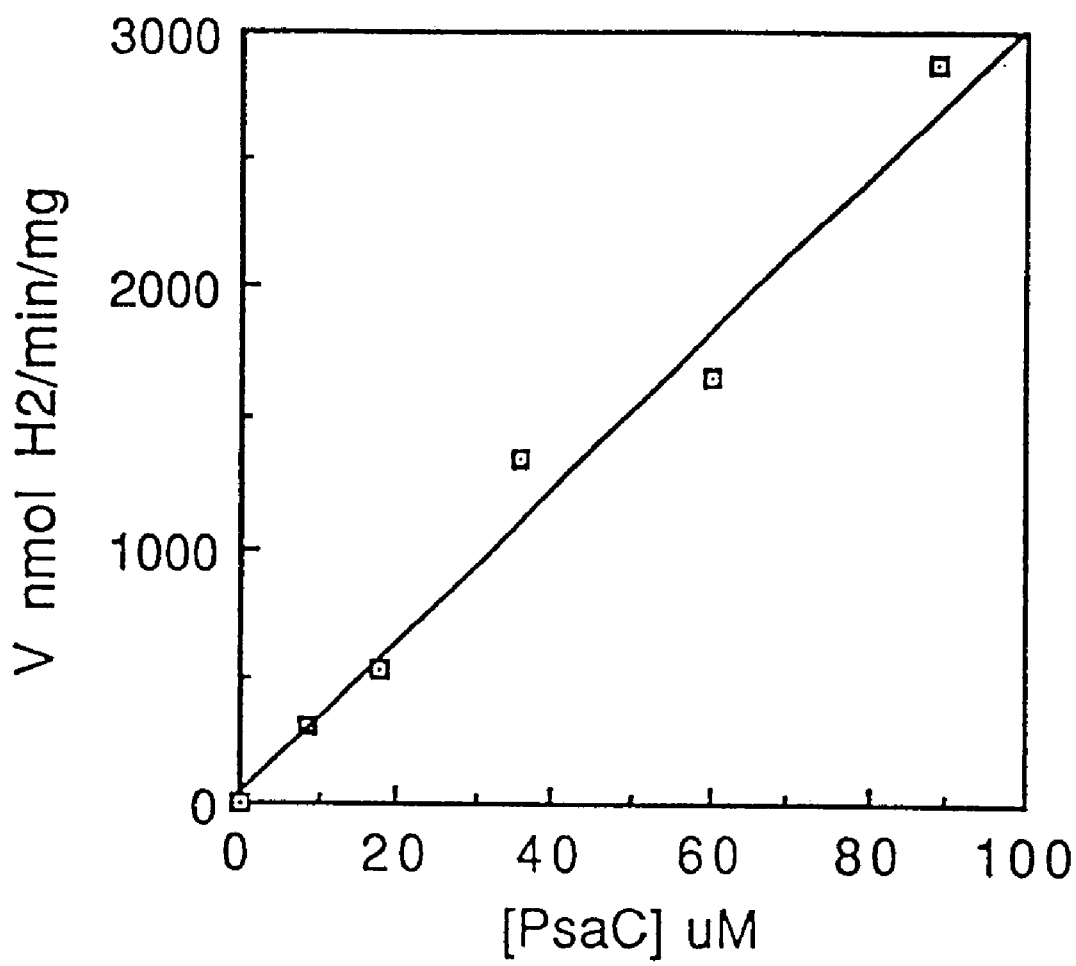
FIG. 1. Dependence of molecular hydrogen production rate on PsaC concentration with *C. pasteurianum* hydrogenase I in 50 mM Tris-HCl, pH 8.0, 5 mM sodium dithionite per 1.5 ml volume.

The present invention is directed to a process for the production of hydrogen gas. The process uses a hydrogenase enzyme and components of the photosynthetic apparatus from an oxygen-producing photosynthetic organism. Previous processes for molecular hydrogen production that used hydrogenase and the photosynthetic apparatus required a exogenous electron carrier to transport electrons from photosystem I to hydrogenase. This can result in a less efficient process since the electrons cannot be transferred directly to the hydrogenase. It also depends on the additional of an exogenous electron carrier. The present process omits the exogenous electron carrier and is more efficient since in the absence of the exogenous electron carrier, the losses of electron flow to destinations other than molecular hydrogen production via hydrogenase can be minimized or negated.

The term "electron carrier" is used herein to refer to a compound, such as a protein, a chemical, or the like that can readily be reduced and oxidized. That is, one or more electrons or electrons and protons can be reversibly added to the compound.

The term "exogenous electron carrier" is used here in to mean a protein or chemical that can function as an electron carrier that is not part of the native photosytem I complex.

The present invention relates to a composition that generates molecular hydrogen and to methods for producing molecular hydrogen. In one aspect of this invention, the composition comprises:

(1) A photosystem I complex from a green plant or other oxygen-producing photosynthetic organism such as, but not limited to, a cyanobacterium or green algae. For a review of photosystem I, see Golbeck and Bryant (*Curr. Topics Bioenergetics* 16:81, 1991).The photosystem I complex preferably includes the $F_A$ and $F_B$ iron-sulfur clusters, which function as the terminal bound electron acceptors in the photosystem I complex and are bound to the PsaC polypeptide. The photosystem I complex may be in the native thylakoid membrane along with photosystem II and the rest of the photosynthetic electron transport chain, or it can be provided in a detergent-solubilized form. Methods for isolating native thylakoid membranes from photosynthetic organisms are known and a preferred method is provided in the publication of Kuwabara, T. and Murata, N. (*Plant Cell Physiol.* 23: 533–539, 1982). Purified thylakoids are quantitated and expressed as a particular amount of chlorophyll. Methods for quantitating chlorophyll are known and an exemplary method used in this invention follows the methods of Arnon (see *Plant Physiol.* 24:1, 1949). Methods for obtaining isolated photosystem I in a detergent solubilized form is also known and an exemplary method is disclosed by Evans, M. D. W. et al. (*Biochem J.* 162:75–85, 1977).

(2) An electron donor capable of donating electrons to photosystem I. Electron donors can be direct electron donors, indirect electron donors, or both. A direct electron donor can directly reduce $P700^+$ (i.e., the oxidized special chlorophyll pair of photosystem I). An indirect electron donor, as used in this disclosure, refers to electron donors that reduce other components of the photosynthetic electron transfer chain, and the natural photosynthetic electron transfer chain reduces photosystem I. This can be a very low potential electron donor (i.e., with an $E_0'$ less than about −400 mV), capable of reducing the $F_A$ and $F_B$ iron-sulfur clusters of photosystem I in the dark in aqueous solution at close to neutral pH. Or it can be a higher potential electron donor such as, one or more of, for example, dithiothreitol, ascorbic acid, 2,6-dichlorophenol indophenol or N,N,N',N'-tetramethyl-p-phenylenediamine (all commercially available). If a higher potential electron donor such as dithiothreitol or ascorbic acid is used, photosystem I must be illuminated with visible light in order for it to catalyze the reduction of the $F_A$ and $F_B$ iron-sulfur clusters (see Golbeck and Bryant, supra). Water can also be used as an indirect electron donor to photosystem I if thylakoids having a functional photosystem II and functional photosynthetic electron transfer chain are used in place of solubilized photosystem I. In that case, water would donate its electrons to photosystem I through photosystem II and the photosynthetic electron transfer chain. In one preferred embodiment of this invention, thylakoids, hydrogenase and water can be used where water acts as an electron donor. In another embodiment of this invention thylakoids, a hydrogenase and a combination of electron donors is used. Preferably a combination of electron donors such as dithiothreitol and ascorbic acid is used and still more preferably, a combination of about 50 mM dithiothreitol and about 2 mM ascorbic acid is used.

(3) At least one hydrogenase enzyme capable of accepting electrons directly from the photosystem I core complex and without intending to limit the scope of the invention, the hydrogenases of this invention are preferably capable of accepting electrons directly from the $F_A$ and $F_B$ iron-sulfur clusters of the photosystem I complex. Hydrogenases have been described in the literature and for a review see Przybyla et al. (*FEMS Microbiol. Revs.* 88:109, 1992) and Adams, M. W. W. (*Biochim. Biophys. Acta* 1020:115, 1990). Methods are provided in the examples for testing for whether or not a particular hydrogenase is capable of accepting accepting electrons directly from photosystem I. As used here, hydrogenases are biological catalysts able to accept electrons from suitable electron donors and combine the electrons with two $H^+$ ions to make molecular hydrogen. The hydrogenases can be purified from cells known to contain hydrogenases, (see methods provided in the Examples section), or the hydrogenases can be supplied in a recombinant form. Methods for cloning hydrogenases are known (see for example, Wu and Mandrand, *FEMS Microbiol. Rev.* 104:243, 1993 and Friedrich and Schwartz, *Ann. Rev. Microbiol.* 47:351, 1993). The hydrogenases used in this invention preferably are not inhibited by the presence of dissolved oxygen.

However, if a hydrogenase is used that is inhibited by dissolved oxygen, it may be necessary to remove oxygen. The removal of oxygen can be performed in a number of ways. For example, if dithionite or high concentrations of dithiothreitol (e.g., 50 mM dithiothreitol) are used as electron donors, these will react with dissolved oxygen to remove it. If water is used as electron donor to thylakoids, oxygen will be produced by photosystem II and 5 mM glucose plus glucose oxidase (3 µg/ml, Sigma, St. Louis, Mo.) can be included in the reaction mix to rapidly remove oxygen as it is produced. It is also possible to maintain anaerobic conditions by bubbling the solution with an inert gas such as nitrogen or argon.

This invention, unlike previous methods for producing molecular hydrogen using a photosynthetic apparatus, does not require an exogenous electron carrier to accept electrons from photosystem I and donate them to hydrogenase. Exogenous electron carriers have been used in previous biological molecular hydrogen production processes using photosystem I and hydrogenase (see references cited in "Background of the Invention"). In contrast, in the methods of this invention, molecular hydrogen is produced by direct electron transfer from photosystem I to hydrogenase.

The present process can be used for producing molecular hydrogen in vitro, or, if a suitable hydrogenase is present in the cytoplasm of a cyanobacterial cell or in the chloroplast stroma in the cell of a eucaryotic photosynthetic organism, could be used for producing molecular hydrogen in a living whole cell or a stabilized non-living cell. Cells can be engineered by the expression of a recombinant hydrogenase from a cloned gene with expression of the gene in the cytoplasm of a cyanobacterium, for example. The hydrogenase is one that would accept electrons directly from photos stem I. The hydrogenase would then be able to make contact with the cytoplasmic side of the integral membrane photosystem I complex.

Preferably, where an in vitro system is used, in order to demonstrate that molecular hydrogen production arises in this system from direct electron transfer from photosystem I to hydrogenase and is not due to an exogenous electron carrier transferring electrons from photosystem I to hydrogenase, the components are first purified from any exogenous electron carrier proteins, in particular ferredoxin. The particular procedures used to purify thylakoids and photosystem I from spinach, hydrogenase I from *C. pasteurianum* and hydrogenase from Rhodococcus sp. MR11 are described in the examples below. Other methods for purifying thylakoids and photosystem I are available in the literature and therefore readily obtainable to those of ordinary skill in the art.

The hydrogenase and the photosystem I or thylakoids are mixed together to produce molecular hydrogen. In a preferred embodiment the components of this invention are suspended in a buffered aqueous solution at a pH at which both the photosynthetic components and hydrogenase are active (for example, in a solution of about 2 mM to about 500 mM Tris-HCl, pH 8.0, preferably 30 mM Tris-HCl to 100 mM Tris-HCl, and preferably about 40 mM Tris-HCl), at a temperature at which both hydrogenase and the photosynthetic components are active (generally about 10° C. to about 40° C.), and with an appropriate electron donor. Exemplary electron donors include sodium dithionite (in one example at about 5 mM) or dithiothreitol (for example at about 50 mM) and in another example using a combination of dithiothreitol plus ascorbic acid (for example, about 2 mM ascorbic acid). Other electron donors can be tested in this system without undue experimentation.

Water may also be used as an electron donor with thylakoids but where water is used it is understood that high concentrations of Tris can inhibit the water oxidation system of photosystem I. Therefore, other suitable buffers can be used such as a phosphate buffered system, for example a 20 mM sodium phosphate at about pH 6.5. If a high potential electron donor, such as dithiothreitol, ascorbic acid, or water, is used, the system is illuminated. In general any illumination sufficient to excite photosystem I can be used. In the examples, provided below, a 150 W light source positioned about 8 centimeters (cm) from the reaction vessel was used and the vessel was fully illuminated by the light source.

Optionally, 5 millimolar (mM) glucose plus 3 $\mu$g per ml glucose oxidase (Sigma Chemical) may also be included to scavenge oxygen, particularly if water is used as the electron donor. Catalase may also be added to remove the hydrogen peroxide produced by glucose oxidase.

The concentration of hydrogenase used in the assay is preferably about 30 to about 1500 units of hydrogenase and preferably about 40 to about 50 units of hydrogenase. It will be understood by those of ordinary skill in the art that the amount of hydrogenase added to the system can affect the efficiency of molecular hydrogen production. In general, a unit of hydrogenase is defined as the amount of hydrogenase that catalyzes production of one micromole of molecular hydrogen per minute under standard conditions such as 2 mM methyl viogen and 5 mM dithionite in pH 7 buffered solution at about 30° C. The concentrations of hydrogenase enzyme catalyzing molecular hydrogen production are higher than those disclosed by Benemann et al. (supra). While not intending to limit the scope of this invention, when the lower concentrations of hydrogenase and photosystem I are used, the hydrogenase and photosystem I may only rarely make direct contact.

The concentrations of chlorophyll preferably used in one embodiment including thylakoids at least one hydrogenase and an electron donor are preferably at least about 30 $\mu$g/ml chlorophyl and preferably about 30 $\mu$g/ml to about 200 $\mu$g/ml and in a preferred embodiment about 50 $\mu$g/ml to about 100 $\mu$g/ml.

The concentrations of photosystem I preferably used in one embodiment including photosystem I, at least one hydrogenase and an electron donor are approximately at least about 0.5 $\mu$M photosystem I and preferably about 0.5 $\mu$M to about 30 $\mu$M photosystem I and still more preferably in an amount where photosystem I is fully saturated by light.

In another aspect of this invention, a dithionite-reduced photosystem I molecular hydrogen production method is used (see Example 3). Here, preferably at least about 5 $\mu$M photosystem I and preferably about 5 $\mu$M to about 1 mM photosystem I and still more preferably about 13 $\mu$M to about 1 mM photosystem I is used. In this system, preferably less than 1 unit of hydrogenase is used and preferably about 0.5 mM to about 20 mM of an electron donor such as dithionite.

The components are added to form a composition in a closed vessel. It is contemplated that the reaction can be scaled up or down without undue experimentation. Preferably $O_2$ is not present and in one embodiment the closed vessel lacks head space and in another embodiment there is a head space fixed to a gas collection apparatus. Molecular hydrogen is preferably measured amperimetrically. Such methods are known in the art and a preferred example for measuring molecular hydrogen is provided by Sweet et al. (Anal. Biochem. 107:337, 1980). Bubbles of hydrogen forming in the system over time can be trapped and isolated from other gases, for example, using a semi-permeable membrane that permits hydrogen flow but excludes other gases. Alternatively, the solution can be flushed with air or nitrogen gas to promote egress of molecular hydrogen into the gas space. Preferably the vessel used for the reaction of this invention is translucent to permit the excitation of the photosynthetic system by light and preferably the vessel is impermeable to hydrogen gas.

All references and publications cited herein are expressly incorporated by reference into this disclosure. Particular embodiments of this invention will be discussed in detail and reference has been made to possible variations within the scope of this invention. There are a variety of alternative techniques and procedures available to those of skill in the art which would similarly permit one to successfully perform the intended invention.

EXAMPLE 1

Light-Dependent Molecular Hydrogen Production with Thylakoids and *Clostridium pasteurianum* Hydrogenase I To prepare thylakoids from chloroplasts that were completely broken and washed of ferredoxin, 200 g deribbed spinach was ground in a Waring blender in 500 ml of 50 mM Tris-HCl, pH 8.1, and the slurry was filtered through about 4 layers of cheesecloth. Debris and unbroken chloroplasts were pelleted by centrifugation at 2,000 rpm for 2 min in a Beckman JA-10 rotor (Beckman Instruments, Brea, Calif.). The supernatant was removed and centrifuged at 8,000 rpm for 20 min to pellet thylakoids. The pellet was resuspended in 25 mM Tris-HCl, pH 8.1, to osmotically burst any unbroken chloroplasts, then centrifuged at 2,000 rpm for 2 min. The supernatant was removed, 4 M NaCl was added to it to a final 0.5 M, and the supernatant was centrifuged at 8,000 rpm for 20 min. The pellet was washed once in 25 mM Tris-HCl, pH 8.1, and resuspended in 25 mM Tris-HCl, pH 8.1.

*C. pasteurianum* Winogradski 5 (ATCC 6013 American Type Culture Collection, Rockville Md.) was grown under nitrogen at 35° C. in 6.5 mM potassium phosphate, pH 7.0, 25 mM ammonium acetate, 20 g/L sucrose, 0.2 mM $MgSO_4$, 20 $\mu$M ferrous sulfate-EDTA, 2 mM sodium dithionite. As the pH dropped below pH 6.0 during growth, the pH was adjusted up to approximately pH 6.5 using solid dibasic potassium phosphate or 5 M KOH. Cells were harvested and resuspended in 100 mM Tris-HCl, pH 8.3, 2 mM sodium dithionite, and broken by lysozyme digestion followed by one freeze-thaw cycle.

Hydrogenase Assay

Hydrogenase activity was assayed by measuring molecular hydrogen production in 50 mM Tris-HCl, pH 8.1, 5 mM sodium dithionite, 1.33 mM methyl viologen at 23° C., with dissolved molecular hydrogen measured amperometrically here and in subsequent examples as described by Sweet et al. *Anal. Biochem* 107, 337 (1980). The experiments were performed in a glass chamber capable of holding a sample volume of 1.5 ml without a head space. A suitable chamber for use with a 1.5 ml sample volume and using an oxygen electrode (see Sweet et al. supra) can be purchased from Gilson Medical Electronics, Inc. (Middleton, Wis.). Those of ordinary skill in the art will recognize that the size of the vessel can be readily scaled up or down. The vessel is preferably sealed with a glass stopper with a narrow channel through it to allow the addition or removal of sample to the reaction mix.

Hydrogenase Purification

All steps in the hydrogenase purification were carried out anaerobically with 2 mM dithionite (Sigma) added to the buffers. Broken cells were centrifuged at 8,000 rpm in a Beckman JA-10 rotor for 20 min to pellet debris. Protamine sulfate (0.5 g in 20 ml water, Sigma) was added to the soluble extract of 75 g cells at 23° C. and centrifuged at 8,000 rpm in a JA-10 rotor for 10 min. The supernatant was dialyzed overnight against 25 mM Tris-HCl, pH 8.3. It was then loaded onto a 2.5×10 cm Bio-Rad DEAE macroprep column (Bio-Rad, Richmond, Calif.) equilibrated with 25 mM Tris-HCl, pH 8.1. The hydrogenase was eluted with a 0–400 mM NaCl gradient (180 ml total volume) in 25 mM Tris-HCl, pH 8.1. In these experiments, hydrogenase eluted at approximately 150 mM NaCl, well separated from ferredoxin, which eluted later. Hydrogenase-containing fractions were pooled and dialyzed against 25 mM Tris-HCl, pH 8.1, then loaded on an identical DEAE column and eluted with the same gradient again. This time, hydrogenase eluted at approximately 325 mM NaCl. Hydrogenase-containing fractions were concentrated to 4 ml by ultrafiltration under nitrogen. Fractions were tested for hydrogenase activity as described above.

Molecular hydrogen production was assayed as follows. Three-hundred µl of anaerobic hydrogenase at 16.9 mg/ml protein (as determined by Bradford, *Anal. Biochem.* 72:248, 1976) with a total activity of about 46 units was injected into 1.2 ml of 25 mM Tris-HCl, pH 8.1, 2 mM ascorbic acid, 50 mM dithiothreitol, 2 µM 3(3,4-dichlorophenyl)-1,1-dimethylurea (DCMU, a photosystem II inhibitor, Sigma), 5 mM glucose, and thylakoids (96 µg chlorophyll, as determined by Arnon, supra). The solution was stirred exposed to air for 20 sec to oxidize dithionite from the hydrogenase solution. Then the solution was sealed with a glass stopper to exclude air. Glucose oxidase (4.5 µg) was injected to remove oxygen. After 2 min in the dark with no molecular hydrogen production, the sample was illuminated with focused light from an intense light source, such as a film projector 150 W bulb. The initial rate of molecular hydrogen production upon illumination was 0.91 nmoles/min. The rate gradually rose until after 33 min of illumination the rate of molecular hydrogen production was about 62 nmoles/min. Turning off the illumination stopped molecular hydrogen production immediately, and molecular hydrogen production immediately resumed when illumination was begun again. Sixty-two nmoles molecular hydrogen production per min is equivalent to 6% of the maximal rate of light-driven electron transfer through photosystem I in these thylakoids measured by oxygen consumption with methyl viologen as electron acceptor. Rates can increase with hydrogenase addition.

With only 30 µl of 16.9 mg/ml hydrogenase solution and 58 µg chlorophyll of thylakoids in a volume of about 1.5 ml., molecular hydrogen production could not be detected in 7 minutes of illumination indicating that molecular hydrogen production was dependant on hydrogenase concentration.

The glucose, glucose oxidase, and DCMU were found to be unnecessary in this system in other assays with the same components.

EXAMPLE 2

Light-Dependent Molecular Hydrogen Production with Isolated Photosystem I and *C. pasteurianum* Hydrogenase I To prepare photosystem I core complex, thylakoids were prepared from spinach as in Kuwabara and Murata *Plant Cell Physiol.* 23, 533 (1982), and resuspended in 20 mM sodium phosphate, pH 6.3, 5 mM $MgCl_2$ at 2 mg chl/ml (300 mg chl total). Triton X-100 (25 mg/mg chl) was added and the thylakoids solubilized for 30 min at 23° C. This was centrifuged at 18,000 rpm for 30 min in a JA-20 rotor. The supernatant was collected and its pH adjusted to 7.5 with 100 mM Tris-HCl, pH 8.3. Tris-HCl, pH 7.5, (100 mM) and water were added to give final concentrations of 20 mM Tris and 10 mM phosphate. This was loaded onto a 2.5×13 cm column of DEAE-macroprep (BioRad) and eluted with a 0–500 mM NaCl gradient in 20 mM Tris-HCl, pH 7.5, 0.2% (w/v) Triton X-100 (180 ml total volume). The green P700-containing fractions were pooled. The P700 was measured according to the methods of Marsho and KOK (*Meth. Enymol.* 69: 280, 1980). Triton X-100 was added to the pooled P700-containing fractions to a final 1.2% (w/v) and this was dialyzed against 20 mM Tris-HCl, pH 7.5, at 4° C. It was then loaded on another 2.5×13 cm DEAE-macroprep column and eluted with the same salt gradient. P700-containing fractions were concentrated to 6 ml by ultrafiltration and passed through a 1.5×40 cm Toyopearl HW55TSK (Tosohaas, Montogeryville, Pa.) column equilibrated with 20 mM Tris-HCl, pH 7.5, 300 mM NaCl, 0.2% Triton X-100. The photosystem I fractions were then dialyzed against 50 mM Tris-HCl, pH 8.0, and concentrated by filtration with a centriprep 3 unit (Amicon Inc., Beverly, Mass.). Both the DEAE and size-exclusion chromatography steps separate spinach ferredoxin from photosystem I.

*C. pasteurianum* hydrogenase I was purified as described in Example 1. Hydrogenase (0.3 ml at 16.9 mg/ml and 9.1 units activity/mg, about 46 units) was mixed with 190 µg chlorophyll of photosystem I (3.6 nmoles P700) in a 1.5 ml reaction volume containing 25 mM Tris-HCl, pH 8.1, 50 mM dithiothreitol, and 2 mM ascorbic acid. It was stirred exposed to air for 20 sec, then sealed in the dark. After 1 min the mix was illuminated. Hydrogen production began immediately and accelerated within 90 sec to 9.9 nmoles molecular hydrogen/min. Molecular hydrogen production was quantitated using the methods of Sweet, et al. (supra). Hydrogen production stopped immediately when the illumination was removed.

Since there were no exogenous electron carriers present in the assay, molecular hydrogen production was occurring by direct electron transfer from photosystem I to hydrogenase.

EXAMPLE 3

Hydrogen Production by Direct Electron Transfer from Dithionite-Reduced Photosystem I or Dithionite-Reduced PsaC Polypeptide to *C. pasteurianum* Hydrogenases I and II The soluble fraction extract from broken *C. pasteurianum* cells was prepared as described in Example 1. Spinach photosystem I core complex was prepared as described in Example 2. Production of $H_2$ gas was observed with dithionite-reduced spinach photosystem I core complex and *Clostridium pasteurianum* broken cell extracts (Table 1). The fact that more $H_2$ production is observed with photosystem I (PSI) than with dithionite alone added to the *C. pasteurianum* extract indicates that the photosystem I is a direct electron donor to the *C. pasteurianum* hydrogenase or hydrogenases and is not transferring electrons through *C. pasteurianum* ferredoxin, which would be fully reduced by dithionite alone. The rate of molecular hydrogen production after subtracting the rate with dithionite alone was approximately proportional to photosystem I concentration up to 1.60 mg chl/ml, indicating that these photosystem I concentrations are not saturating as a substrate for hydrogenase (Table 1).

TABLE 1

Rate of $H_2$ production catalyzed by *C. pasteurianum* extracts (0.9 mg protein) in 40 mM Tris-HCl, pH 8.3, 100 mM NaCl, 5 mM sodium dithionite in a 1.5 ml. volume in the dark.

| Electron Donor | V (nmol $H_2$/hr) |
|---|---|
| dithionite alone 23° C. | 7.2 |
| 13 μM PSI (0.53 mg chl/ml) 23° C. | 14.3 |
| 39 μM PSI (1.60 mg chl/ml) 23° C. | 27.4 |
| 2.66 mM methyl viologen 23° C. | 770 |
| dithionite alone 37° C. | 8.0 |
| 9.75 μM PSI (0.40 mg chl/ml) 37° C. | 30 |
| 19.5 μM PSI (0.80 mg chl/ml) 37° C. | 62 |

Molecular hydrogen production was also observed with purified *C. pasteurianum* hydrogenase I mixed with 5 mM dithionite and photosystem I core complex at 0.96 mg chlorophyll (chl)/ml (22.5 μM P700) in the dark in 50 mM Tris-HCl, pH 8.1 (610 nmol molecular hydrogen producted per min per mg hydrogenase at 23° C.). Only 2 nmol molecular hydrogen per min per mg was observed in the absence of photosystem I when dithionite alone served as electron donor to hydrogenase.

These results indicate that the terminal bound electron carriers on the photosystem I complex serve as immediate electron donors to hydrogenase in this system. The terminal bound electron carriers are the electron carrier components of the PSI core complex that are the final electron carriers on PSI to receive electrons following illumination of PSI. These terminal bound electron carriers are the $F_A$ and $F_B$ iron-sulfur clusters on the PsaC polypeptide. To test if the $F_A$ and $F_B$ clusters on PsaC could donate electrons to hydrogenase, free recombinant PsaC protein from Synechococcus sp. PCC 7002 was expressed in *Escherichia coli* BL21 (DE3) from plasmid pET36C, and was purified and reconstituted as in Li et al. (*Biochemistry* 30: 7863, 1991). The purified PsaC was tested for supporting molecular hydrogen production with *C. pasteurianum* hydrogenase I. PsaC at about 18 μM supported about 540 n moles molecular hydrogen production per min per mg hydrogenase (FIG. 1). This can be compared with the assay above where 22.5 μM photosystem I supported 610 nanomoles (nmol) molecular hydrogen production per min per mg hydrogenase I. Thus, dithionite-reduced PsaC, at approximately the same molar concentration as diothionite-reduced photosystem I, supported approximately the same rate of molecular hydrogen production with *C. pasteurianum* hydrogenase I.

In FIG. 1 the dependence of molecular hydrogen production rate on PsaC concentration was plotted based on the results of assays using 50 mM Tris-HCl, pH 8.0, 5 mM sodium dithionite at 23° C. The concentration of reconstituted PsaC was calculated using $\epsilon_{410}$=15 mM$^{-1}$ (Wynn and Malkin, *FEBS Lett.* 229:293, 1988). The data in FIG. 1 and in Table I both indicate that PsaC and photosystem I are not saturating as electron donors to hydrogenase I at the concentrations used. The rate of molecular hydrogen production continued to increase with increasing PsaC or photosystem I concentrations.

Electron paramagnetic resonance (EPR) spectroscopy demonstrated that the $F_A$ and $F_B$ iron-sulfur clusters are reduced by dithionite in the dark in the spinach photosystem I preparation and thus are available to be electron donors to hydrogenase. The EPR spectrum of photosystem I core complex in 50 mM Tris-HCl, pH 8.0, 5 mM dithionite, in the dark was acquired. EPR was performed using the following conditions: temperature 18 Kelvin, microwave frequency 9.230 Ghz, microwave power 0.6 mW, gain 8,000, scan time 4 min, time constant 0.128 sec, modulation amplitude 10 G, modulation frequency 100 kHz. The spectrum matched the reported spectrum of the $F_A$ and $F_B$ clusters, with the g=1.89 peak arising in part from interaction between the two reduced clusters (for guidance on interpreting results of EPR studies of photosystem I see Golbeck and Bryant, (*Current Topics in Bioenergetics* 16: 83, 1991). Double integration of the spectrum, excluding the g=2.0 radical signal and comparison to a $Cu^{2+}$-ethylenediamine tetraacetic acid standard gave a spin concentration of 21 μM, which would be 1.85/P700. One would predict 2 unpaired e$^-$/P700 if $F_A$ and $F_B$ were fully reduced. The amplitude of the spectrum increased by a factor of 1.42 if the sample was illuminated with freezing in liquid nitrogen. That treatment is reported to fully reduce the $F_A$ and $F_B$ clusters (Heathcote et al. *Biochim. Biophys. Acta* 503:333, 1978), which would mean that in the dark they were 70% reduced by dithionite.

To demonstrate that the electron donor to hydrogenase in these assays is the photosystem I core complex and not contaminating ferredoxin, photosystem I was precipitated. Forty percent-saturated ammonium sulfate completely precipitated photosystem I but did not precipitate spinach ferredoxin. The photosystem I preparation was precipitated with 40%-saturated ammonium sulfate and the pellet and supernatant after centrifugation were separately dialyzed (1,100 mw cut-off membrane) against 50 mM Tris-HCl, pH 8.0. The dialyzed product was tested for its ability, when reduced with dithionite, to support molecular hydrogen production with *C. pasteurianum* hydrogenase I. The supernatant had only 12% of the ability to support molecular hydrogen production compared to the starting photosystem I prior to precipitation. If the ability of the photosystem I preparation to support molecular hydrogen production had come entirely from contaminating ferredoxin, this value should have been close to 100%. Therefore, molecular hydrogen production observed with dithionite-reduced photosystem I core complex and *C. pasteurianum* hydrogenase I did not arise from ferredoxin contaminating the photosystem I preparation. Photosystem I was acting as the electron donor to hydrogenase.

One approach to demonstrating that the photosystem I core, and specifically the PsaC polypeptide on the photosystem I core, was capable of donating electrons directly to hydrogenase was a reconstitution experiment. Purified photosystem I was stripped of its small extrinsic polypeptides, including PsaC and PsaD, by treatment with 6 M urea followed by size-exclusion chromatography. Then a portion of this urea-stripped PSI was reconstituted with recombinant PsaC and PsaD.

PsaD from Nostoc sp. PCC 8009 was overexpressed from the plasmid pET-3a/D in *E. coli* BL21(DE3) as in Li et al.

(*Biochemistry* 30:7863 1991). PsaC was expressed from a plasmid in *E. coli*, purified and reconstituted as described above in Example 3. To remove PsaC, PsaD, and other extrinsic polypeptides from native photosystem I, photosystem I was treated with 6 M urea in 50 mM Tris-HCl, pH 8.0, at 0.25 mg chl/ml, concentrated to 5 ml and passed through a 1.5×40 cm Toyopearl HW55TSK column equilibrated with 50 mM Tris-HCl, pH 8.0, 5 M urea. Green colored fractions were then dialyzed against 50 mM Tris-HCl, pH 8.0, 0.05% Triton X-100. For reconstitution, 1.7 ml of 0.94 mg chl/ml urea-stripped photosystem I was mixed with 0.9 mg reconstituted purified PsaC and 3.1 mg purified PsaD in 50 mM Tris-HCl, pH 8.0, 0.05% Triton X-100, incubated 10 min at 23° C. and then filtered and diluted three times with Centricon 100 units (Amicon Co.) to remove unbound PsaC and PsaD. The dithionite-reduced urea-stripped photosystem I was found to support no more $H_2$ production than dithionite alone with *C. pasteurianum* cell extracts. But the photosystem I reconstituted with PsaC and PsaD did support some $H_2$ production, almost as much $H_2$ production as would be predicted by comparison with the rate with a somewhat greater concentration of free PsaC (Table 2). This indicates that it is the PsaC polypeptide of photosystem I that acts as the electron donor to the hydrogenase in these assays.

TABLE 2

Ability to support $H_2$ production of urea-stripped and reconstituted photosystem I (PSI). $H_2$ production was catalyzed by *C. pasteurianum* extracts (30 μg/ml) in 50 mM Tris-HCl, pH 8.0, 5 mM sodium dithionite.

| Electron Donor | V (μmol $H_2$/min/ml) |
|---|---|
| dithionite alone | 1.6 |
| 12.4 μM urea-stripped PSI | 1.7 |
| 12.4 μM urea-stripped PSI reconstituted with PsaC and PsaD | 2.5 |
| 21 μM free PsaC | 4.4 |

Like hydrogenase I, partially purified hydrogenase II of *C. pasteurianum* was also able to produce $H_2$ with dithionite-reduced PSI (3.2 nmol $H_2$ per min per mg hydrogenase II at 23° C.). Here, interestingly, the velocity of molecular hydrogen production increased when assayed in 2 M urea, whereas there was a decrease in velocity in 2 M urea when ferredoxin was the electron donor. This again supports the idea that the photosystem I core, not contaminating ferredoxin, was the electron donor. Partially purified hydrogenase II for those assays was collected as fractions based on $H_2$ oxidizing activity eluting before hydrogenase I activity from the first DEAE column during the purification of hydrogenase I. Hydrogenase II was distinguished from hydrogenase I by its higher ratio of hydrogen oxidization to hydrogen production activity.

EXAMPLE 4

Figure 2:
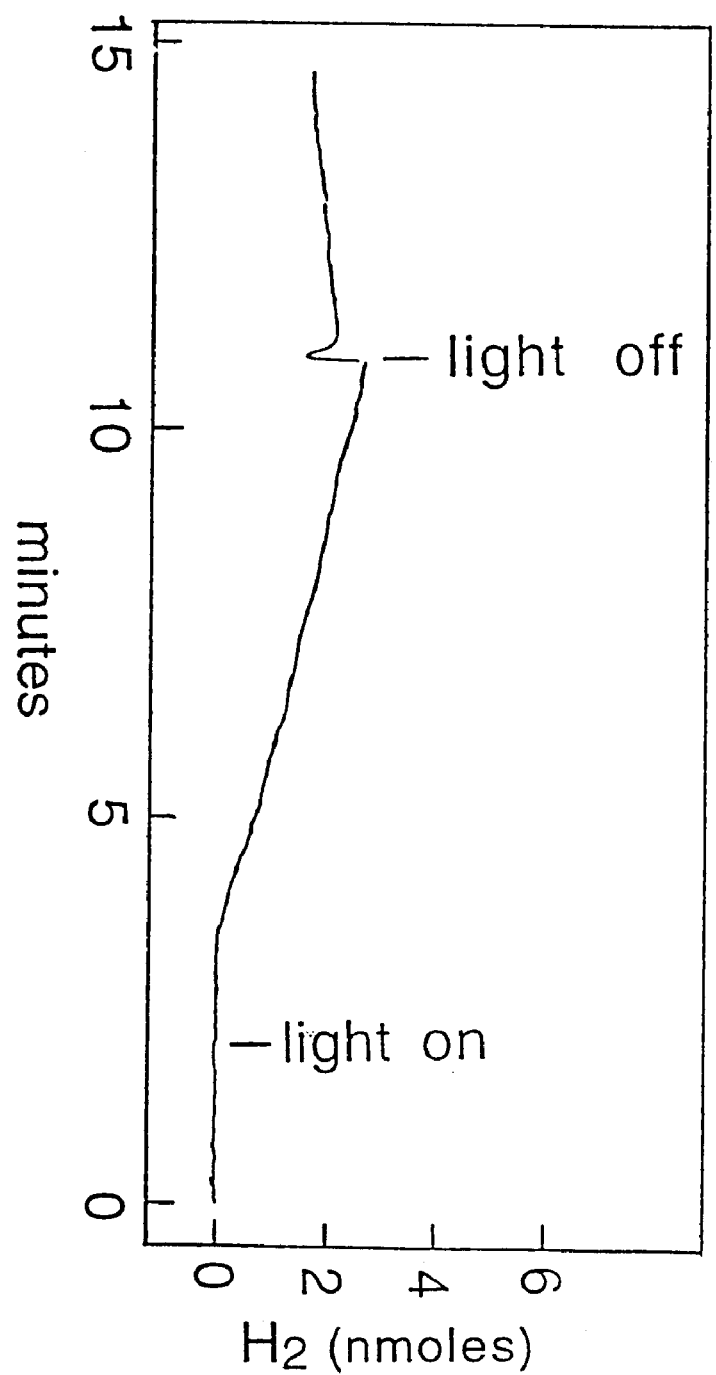
FIG. 2. Light-dependent molecular hydrogen production with thylakoids and Rhodococcus sp. MR11 hydrogenase.

Light-Dependent Molecular Hydrogen Production with Thylakoids and Rhodococcus sp. MR11 Hydrogenase Light-driven molecular hydrogen production was observed with thylakoids and purified Rhodococcus sp. MR11 hydrogenase, an enzyme that is not affected by oxygen (FIG. 2). Rhodococcus sp. MR11 was grown at 30° C. in minimal medium as described by Schneider et al. (*Eur. J. Biochem.* 142:75, 1984) at pH 7.0 supplemented with 0.2% glycerol and 0.4% fructose until the hydrogen oxidizing activity of the culture stopped increasing (approximately 36 hours after the culture reached stationary phase). Rhodococcus sp. MR11 hydrogenase was purified as in Schneider et al. (supra). The molecular hydrogen production activity of this hydrogenase preparation assayed in 50 mM Tris-HCl, pH 7.5, 5 mM $MgSO_4$, 0.5 mM $NiCl_2$, 5 mM sodium dithionite, 1.33 mM methyl viologen at 23° C. was 2.5 μmoles molecular hydrogen per min per mg protein.

The assay shown in FIG. 2 used an assay volume of 1.5 ml containing thylakoids (145 μg chl), Rhodococcus sp. MR11 hydrogenase (0.28 mg), 50 mM Tris-HCl, pH 7.5, 5 mM $MgSO_4$, 2 mM ascorbic acid, and 50 mM dithiothreitol at 23° C. Since there were no exogenous electron carriers added to this system, the molecular hydrogen production observed was again provided from direct electron transfer from photosystem I in the thylakoids to hydrogenase.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

What is claimed is:

1. A method for producing molecular hydrogen comprising combining: (a) photosystem I complex from a photosynthetic organism, (b) at least one hydrogenase enzyme which catalyzes the production of molecular hydrogen, and (c) an electron donor which donates electrons to photosystem I, wherein molecular hydrogen production occurs by direct electron transfer from the photosystem I complex to the hydrogenase.

2. The method of claim 1 wherein the photosystem I is present in thylakoids and the electron donor is one of the electron donors naturally present in the cell and used in the natural photosynthetic electron transfer process as electron donor to photosystem I.

3. The method of claim 1, wherein the electron donor donates electrons indirectly to photosystem I.

4. The method of claim 1, wherein the hydrogenase is purified from a cell.

5. The method of claim 1 wherein the electron donor is a mixture of dithiothreitol and ascorbic acid.

6. The method of claim 1 further comprising exposing photosystem I to light.

7. A method for producing molecular hydrogen comprising combining: (a) photosystem I complex from a photosynthetic organism, (b) at least one hydrogenase enzyme which catalyzes the production of molecular hydrogen, and (c) an electron donor which donates electrons to photosystem I, wherein ferredoxin is absent or at a sufficiently low concentration and the hydrogenase is at sufficiently high concentration, so that molecular hydrogen production occurs by direct electron transfer from the photosystem I complex to the hydrogenase at the rate of at least 3.1 micromoles per hour per mg chlorophyll.

8. The method of claim 7 wherein the photosystem I complex is present in thylakoids and the electron donor is one of the electron donors naturally present in the cell and used in the natural photosynthetic electron transfer process as electron donor to photosystem I.

9. The method of claim 7, wherein the electron donor donates electrons indirectly to photosystem I.

10. The method of claim 7, wherein the hydrogenase is purified from a cell.

11. The method of claim 7 wherein the electron donor is a mixture of dithiothreitol and ascorbic acid.

12. The method of claim 7 further comprising exposing the photosystem I complex to light.

13. A method for producing molecular hydrogen comprising combining: (a) photosystem I complex from a photosynthetic organism, (b) at least one hydrogenase which catalyzes the production of molecular hydrogen, and (c) an electron donor which donates electrons to photosystem I, wherein at least 49.6% of the molecular hydrogen production occurs by direct electron transfer from the photosystem I complex to the hydrogenase.

14. The method of claim 13 wherein the photosystem I of the combination step is present in thylakoids and the electron donor is one of the electron donors naturally present in the cell and used in the natural photosynthetic electron transfer process as electron donor to photosystem I.

15. The method of claim 13, wherein the electron donor donates electrons indirectly to photosystem I.

16. The method of claim 13 wherein the electron donor is a mixture of dithiothreitol and ascorbic acid.

17. The method of claim 13 further comprising exposing photosystem I to light.

18. A method for producing molecular hydrogen comprising combining in a mixture: (a) photosystem I complex from a photosynthetic organism, (b) at least one hydrogenase enzyme which catalyzes the production of molecular hydrogen, and (c) an electron donor which donates electrons to photosystem I;

wherein molecular hydrogen production occurs by direct electron transfer form the photosystem I complex to the hydrogenase; and wherein the mixture does not comprise ferredoxin.

* * * * *